US006514941B1

(12) United States Patent
Tolton, II et al.

(10) Patent No.: US 6,514,941 B1
(45) Date of Patent: Feb. 4, 2003

(54) METHOD OF PREPARING A CASEIN HYDROLYSATE ENRICHED IN ANTI-HYPERTENSIVE PEPTIDES

(75) Inventors: J. Kelly Tolton, II, Oneonta, NY (US); Ram Nimmagudda, Oneonta, NY (US); Steven D. Braun, Fraser, NY (US); Michael Primmer, Oneonta, NY (US); Frans van der Veerdonk, Rosmalen (NL)

(73) Assignee: Campina Melkunie B.V., Zaltbommel (NL)

( * ) Notice: Subject to any disclaimer, the term of this patent is extended or adjusted under 35 U.S.C. 154(b) by 0 days.

(21) Appl. No.: 09/465,753

(22) Filed: Dec. 17, 1999

Related U.S. Application Data

(60) Provisional application No. 60/169,989, filed on Dec. 10, 1999.

(51) Int. Cl.[7] .......................... A61K 38/00; A01N 37/18; C12P 21/06
(52) U.S. Cl. ........................ 514/14; 514/2; 530/316; 435/68.1
(58) Field of Search .................. 435/68.1; 530/316; 514/2, 14

(56) References Cited

U.S. PATENT DOCUMENTS

| 4,161,520 | A | | 7/1979 | Osborne et al. |
| 4,361,564 | A | | 11/1982 | Edwards |
| 4,816,398 | A | | 3/1989 | Brule et al. |
| 5,037,957 | A | | 8/1991 | Grubb et al. |
| 5,112,812 | A | | 5/1992 | Samuelsson et al. |
| 5,314,873 | A | | 5/1994 | Tomita et al. |
| 5,486,461 | A | | 1/1996 | Nielsen |
| 5,703,212 | A | * | 12/1997 | Sugai et al. ............... 530/360 |

FOREIGN PATENT DOCUMENTS

| WO | WO 95/28425 | 10/1995 |
| WO | WO 99/19354 | 4/1999 |
| WO | WO 99/31129 | 6/1999 |
| WO | WO 99/35246 | 7/1999 |

OTHER PUBLICATIONS

Karaki, Antihypertensive effect of Tryptic Hydrolysate of Milk Casein in Spontaneously Hypertensive Rats, Comp. Biochem.Physiol.vol. 96C, No.2, pp. 367–371, Mar. 1990.*
JP05176714 — Abstract.
JP8269088 A 961015 — Abstract.
JP6128287 A 940510 — Abstract.
WO9102539 A — Abstract.
JP04169598 — Abstract.
JP9121855 — Abstract.
Madsen et al, "Hydrolysis of milk protein by a *Bacillus licheniformis* protease specific for acidic amino acid residues", Journal of Food Science 62(3):579–582 (1997) — Abstract.
Park et al, "Identification of peptides derived from . . . proteolytic enzymes", Korean Journal of Dairy Science 18(4):237–246 (1996) — Abstract.
Queiroz Macedo et al, "Caseinolytic specificity of cardosin, an aspartic protease from the cardoon *Cynara cardunculus* L.: action on bovine ALPHAs–and BETA–casein and comparison with chymosin", Journal of Agricultural and Food Chemistry 44(1):42–47 (1996) — Abstract.
Beeby, R., "The proteolysis of casein by immobilized preparations of ALPHA–chymotrypsin, chymosin and a fungal protease", Dairy Res. Lab, CSIRO Div. of Food Res., Highett, New Zealand Journal of Dairy Science and Technology 14(1):1–11 (1979) — Abstract.

* cited by examiner

Primary Examiner—Christopher R. Tate
Assistant Examiner—Randall Winston
(74) Attorney, Agent, or Firm—Nixon & Vanderhye P.C.

(57) ABSTRACT

The present invention relates, in general, to a casein hydrolysate, and, in particular, to a method of preparing a casein hydrolysate enriched in antihypertensive peptides.

8 Claims, 6 Drawing Sheets

Fig. 1A

Molecular Weight Determination of Proteins Hydrolysates

PURPOSE

This is a test method to analyze molecular weight of protein hydrolysates and raw materials.

EQUIPMENT

1. Isocratic HPLC system with UV detector, autosampler, Waters Millenium Data Acquisition Software
2. Progel TSK-G2000SWXL 7.8 mm x 30 cm (Supelco)
3. Guard Column - Progel TSK SWXL (Supelco)
4. Balance - 4 decimal place
5. Vacuum pump
6. Micro Pipette (10-1000 µl) with tips

MATERIALS

1. HPLC Grade Acetonitrile (Fisher)
2. Triflouroacetic Acid (Fisher)
3. HPLC Grade Water
4. Carbonic Anhydrase (standard) (Sigma)
5. Ribonuclease A (standard) (Sigma)
6. Aprotinin (standard) (Sigma)
7. Insulin (standard) (Sigma)
8. Bacitracin (standard) (Sigma)
9. Phenylalanine (standard) (Sigma)
10. Filtration Apparatus
11. Vacuum & Erlenmeyer flasks
12. Volumetric flasks - 10ml
13. Graduated cylinder - 1000ml
14. Autosampler vials with caps
15. Disposable transfer pipets.

SOLUTIONS

1. Column Solvent
    a. Add 700ml HPLC grade water to a 1000ml erlenmeyer flask.
    b. Add 300ml acetonitrile.
    c. Add 1ml trifluoroacetic acid.
    d. Mix well.
    e. Filter solvent through a 0.45µm filter and degas prior to use. Use within one week.

2. Standard Mix A
    a. Add 40mg carbonic anhydrase, aprotinin, bacitracin and phenylalanine to a beaker.

Fig. 1B b.    Add 80ml column solvent and mix well.
    c.    Aliquot to autosampler vials and store frozen indefinately.

3. Standard Mix B
    a.    Add 20mg ribonuclease A and insulin to a beaker.
    b.    Add 40ml column solvent and mix well.
    c.    Aliquot to autosampler vials and store frozen indefinately.

INSTRUMENT PARAMETERS

Flow rate: 1.0 ml/min.

Detector: 214 nm

Run Time: 20 min.

Condition column with column solvent at a flow rate of 1.0 ml/min. until a stable baseline is reached.

PROCEDURE

1. Add 10mg protein to a 10ml volumetric flask.
2. qs to 10ml with column solvent.
3. Transfer sample to auto sampler vials and cap.
4. Inject 20µl of each standard and sample into HPLC.
5. Use Millenium GPC option software to quantitate data.

Report:

1. Area % in ranges

| | |
|---|---|
| > 10000 | daltons |
| 10000 - 5000 | daltons |
| 5000 - 2000 | daltons |
| 2000 - 1000 | daltons |
| 1000 - 500 | daltons |
| < 500 | daltons |

2. Average molecular weight.

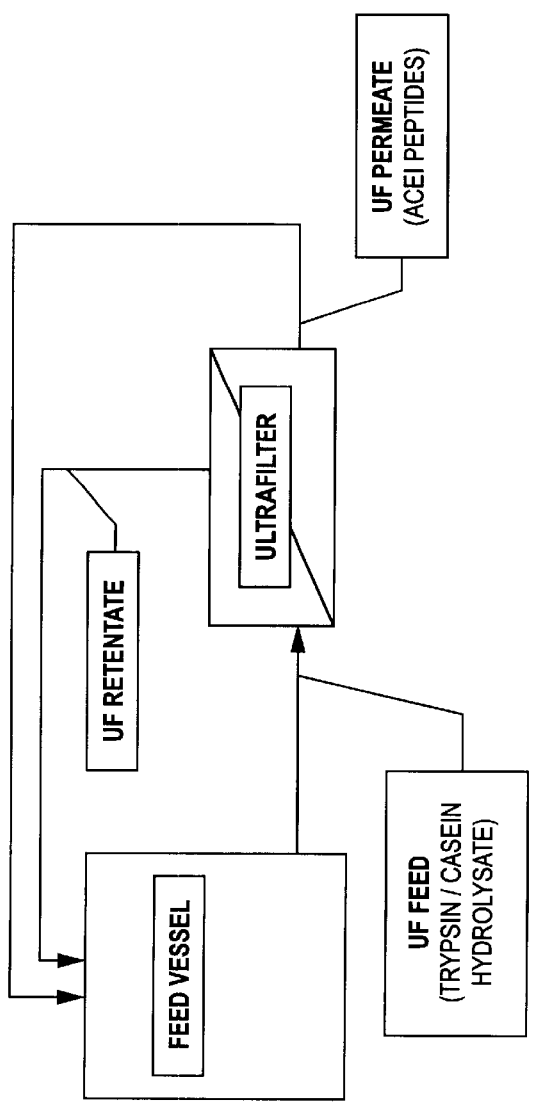
Fig. 2A UF Start-Up
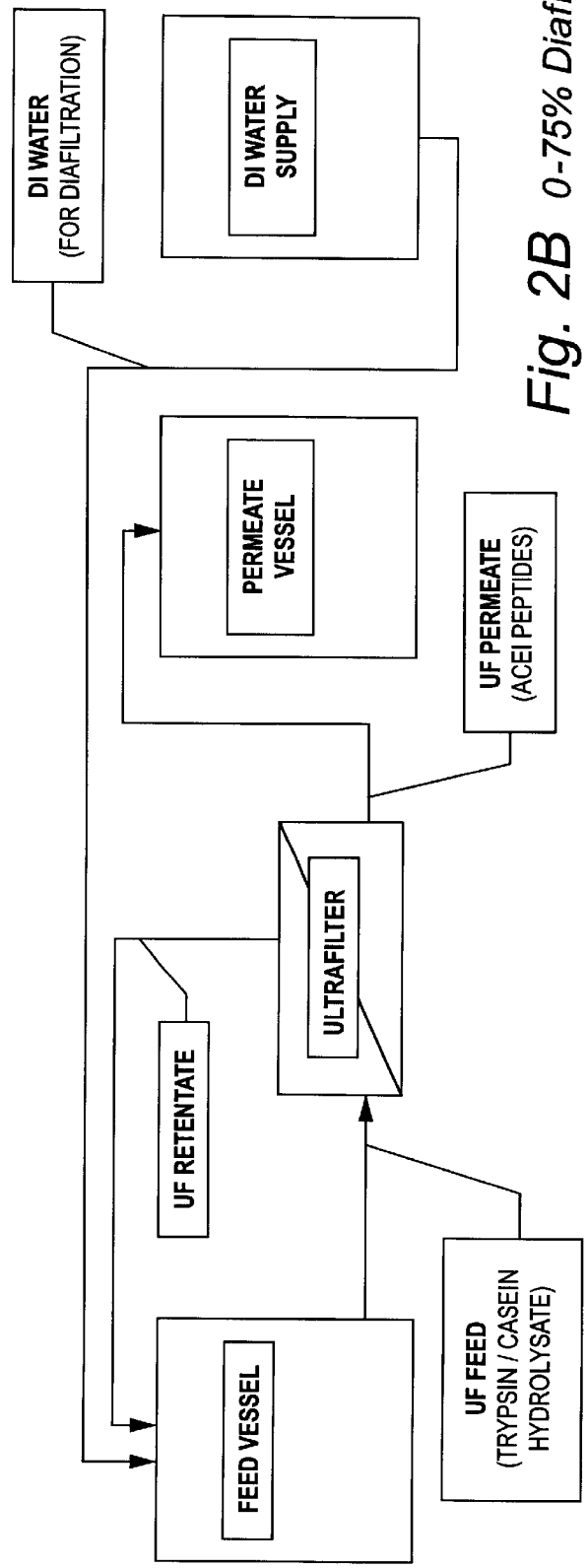
Fig. 2B 0-75% Diafiltration

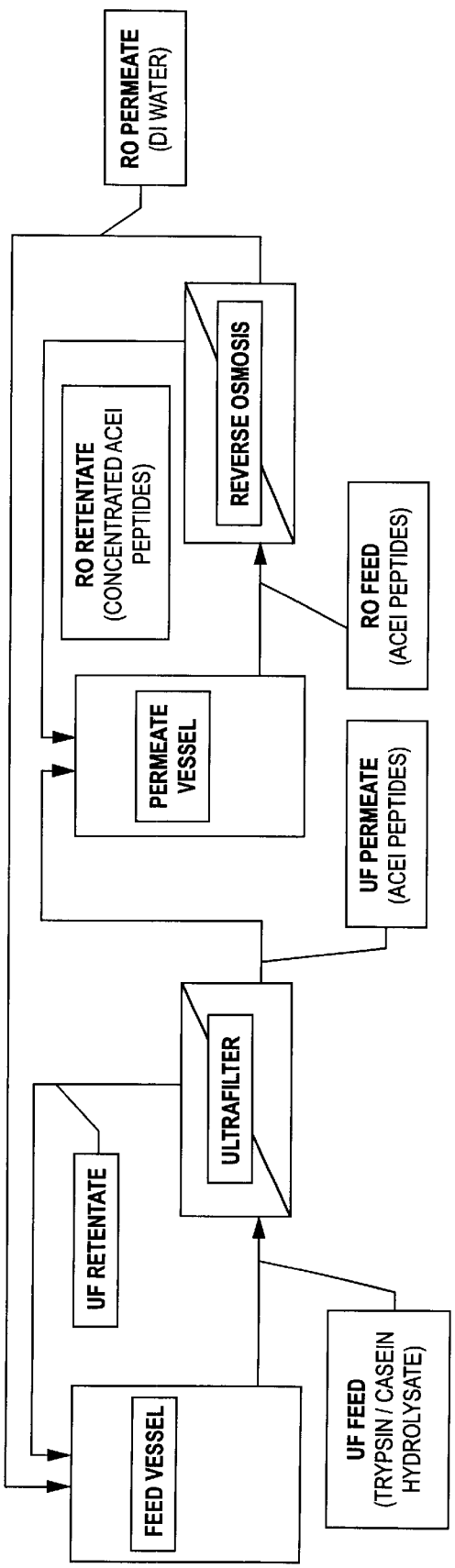
*Fig. 2C* 75-400% Diafiltration
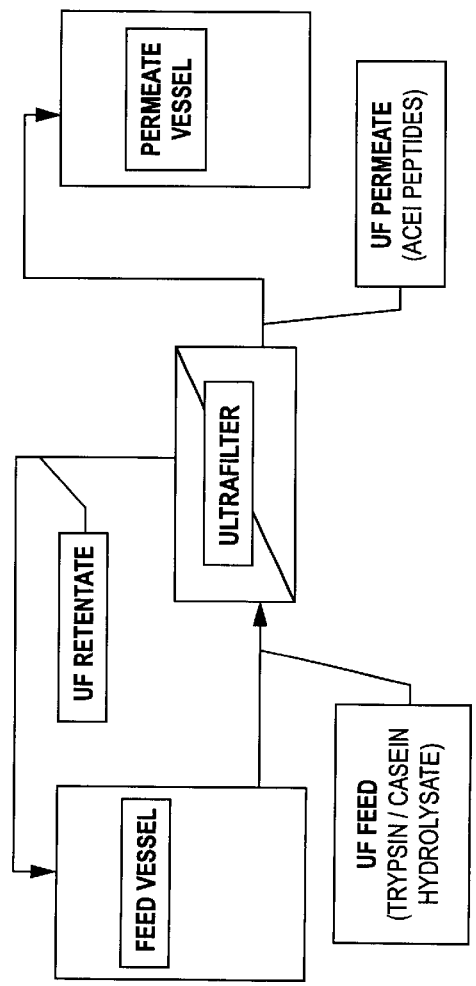
*Fig. 2D* End Diafiltration / Retentate Concentration

Fig. 3A

Quantitation of ACEI Peptides

PURPOSE

This is a test method to quantitate total ACE ($C_6$, $C_7$ and $C_{12}$) peptides in the protein hydrolysate.

EQUIPMENT

1. Gradient HPLC system with UV detector, autosampler, Waters Millenium Data Acquisition Software
2. Column: Hi-Pore RP 318 250x4.6
3. Balance - 4 decimal place
4. Vacuum pump
5. Micro Pipette (10-1000 $\mu$l) with tips

MATERIALS

1. Urea
2. C6 Standard
3. C7 Standard
4. C12 Standard
5. HPLC Grade Acetonitrile (Fisher)
6. Triflouroacetic Acid (Fisher)
7. HPLC Grade Water
8. Filtration Apparatus
9. Vacuum & Erlenmeyer flasks
10. Volumetric flasks - 10ml
11. Graduated cylinder - 1000ml
12. Autosampler vials with caps
13. Disposable transfer pipets.

SOLUTIONS

1. Eluent A    1000 ml DI water, 10 ml Acetonitrile, 1 ml TFA
2. Eluent B    400 ml DI water, 600 ml Acetonitrile, 1 ml TFA

INSTRUMENT PARAMETERS

Flow Rate    0.8 ml/min

Fig. 3B

Elution : Gradient

| Minutes | Eluent A(%) | Eluent B(%) |
|---------|-------------|-------------|
| 0       | 85          | 15          |
| 20      | 50          | 50          |
| 60      | 25          | 75          |
| 61      | 0           | 100         |
| 63      | 0           | 100         |
| 64      | 85          | 15          |
| 70      | 85          | 15          |

Detection 220 nm

PROCEDURE

1. Sample preparation – 20 mg protein is dissolved in 8M urea and volume adjusted to 10 ml with 20% Acetonitrile/80% DI water/0.2% TFA

Report:

1. Standards - $C_6$, $C_7$ and $C_{12}$ are prepared at a concentration of 20 mcg/ml in 20% Acetonitrile/80% DI water/0.2% TFA

METHOD OF PREPARING A CASEIN HYDROLYSATE ENRICHED IN ANTI-HYPERTENSIVE PEPTIDES

This application claims the benefit of U.S. Provisional Application No. 60/,169,989, filed Dec. 10, 1999, the entire content of which is hereby incorporated by reference in this application.

TECHNICAL FIELD

The present invention relates, in general, to a casein hydrolysate, and, in particular, to a method of preparing a casein hydrolysate enriched in antihypertensive peptides, to the resulting hydrolysate and to a method of preventing or treating hypertension using same.

BACKGROUND

With the recent changes in eating habits, the incidence of adult diseases, including hypertension and hyperlipemia, is on the increase. There is also a mounting interest in preventive medicine and thus there is an intense search for substances that are both safe and prophylactically effective.

Animal models of diseases such as cerebral stroke (Yamori et al, Jpn. Circ. J. 38:1095 (1974)), myocardial infarction (Yamori et al, Atherosclerosis 42:15 (1982)) and arteriosclerosis have been developed. Using such models, it has been possible to demonstrate that proper nutrition can be an effective preventative even in animals having a genetic predisposition to circulatory diseases.

Experiments involving the use of animal models, namely spontaneously hypertensive rats (SHR) (Okamoto et al, Jpn. Circ. J. 27:282 (1963)) and stroke-prone SHR (SHRSP), have shown that excess intake of sodium chloride promotes high blood pressure, while certain nutrients protect against it. For example, it has been shown that when soybean protein, lysine, taurine, potassium, calcium, magnesium, palmitoleic acid, etc. are administered before the onset of hypertension, or at an early stage after onset and onwards, a prophylactic effect is obtained (Yamori et al, New horizon in preventing cardiovascular diseases, Yamori and Strasser eds., Elsevier, Amesterdam, pp. 1, (1989)).

It has become increasingly clear that substances derived from food proteins can play a variety of physiological roles. Certain of such substances have been shown to have blood cholesterol-lowering activity and antihypertensive activity (Karaki et al, Comp. Biochem. Physiol., 96C, 367, (1990)). Some are available commercially.

Recently, it has been reported that the angiotensin converting enzyme inhibitor (ACEI), captopril, inhibits the onset of stroke in the SHRSP at a dose that is not hypotensive (Ohta et al, Genetic. Hypertens. 218:393 (1992)). However, captopril has adverse side effects, such as inducing a skin rash. Administration of other substances known to be effective for circulatory diseases, particularly cerebral stroke, are also associated with adverse side effects, including induction of blood-pressure fluctuations and the like.

Therefore, from the standpoint of preventive medicine, there is a significant demand for dietary substances that are effective in preventing or delaying the onset of high blood pressure, particularly, cerebral stroke, and that are safe and relatively inexpensive. The present invention provides a method for producing such a substance.

SUMMARY OF THE INVENTION

The present invention relates to a method of preparing a casein hydrolysate that is enriched in the peptides C6, C7 and C12. The product of the present method can be used as a dietary preventative of circulatory diseases, more specifically, high blood pressure and associated diseases. Further, the present product is relatively free of adverse side effects associated with many antihypertensive pharmaceuticals.

Objects and advantages of the present invention will be clear from the description that follows.

BRIEF DESCRIPTION OF THE DRAWINGS

FIGS. 1A and 1B: Molecular weight determination of protein hydrolysates.

FIGS. 2A–D: Ultrafiltration (UF) configuration. FIG. 2A. Ultrafiltration start up. Initially, the UF is run in a recirculation mode as shown, with both retentate and permeate returned to the feed tank for 15–30 minutes. This allows the system to reach an equilibrium where an initial concentration polarization layer is deposited on the membrane surface. (For details see Ultrafiltration and Microfiltration Handbook, M. Cheryan, Technomic Publishing Co. 1998, p265–266.) FIG. 2B. 0–75% Diafiltration. After the initial recirculation, the permeate is saved in a separate vessel and continuous diafiltration is started immediately without any volume concentrate due to product viscosity and subsequent fouling considerations. A separate deionized water supply is used for diafiltration as shown. FIG. 2C. 75–400% Diafiltration. After ~75% diafiltration, the reverse osmosis (RO) can be started to simultaneously concentrate UF permeate and supply deionized water for further diafiltration. Alternatively, however, deionized water can be continuously supplied from an outside source as shown. Diafiltration is continued until 200–600%, with 400% diafiltration being preferred. FIG. 2D. End diafiltration/retentate concentration. When the diafiltration is completed, the retentate can be concentrated to a volume concentration factor of 2 (½ volume). This can occur without irreversible membrane fouling and can result in retentate having >10% total solids (w/w).

Ultrafiltration conditions; Temperature: 49–60° C. (55–60° C. preferred); Inlet Pressure: 2.9–7.9 bar (7.5–7.9 bar preferred); Delta P: 1.0–1.8 bar (1.25–1.70 bar preferred); TMP: 1.5–5.0 bar (3.5–4.5 bar preferred); Recirculation Rate: 20–40 gpm/membrane series (30–35 gpm preferred)(see Koch specification sheet Part#: 0750011, Rev: 2, Date: Apr. 12, 1996).

FIGS. 3A and 3B: Quantitation of ACEI (C6, C7 and C12) peptides.

DETAILED DESCRIPTION OF THE INVENTION

The present invention relates to a method of preparing a composition comprising C6-$\alpha_{s1}$194–199, C7-$\beta$177–183 and C12-$\alpha_{s1}$23–34 peptides—(hereinafter, C6, C7 and C12 peptides, respectively) (see Karaki et al, Comp. Biochem. Physiol. 96C, 367 (1990)). In general, the method comprising solubilizing casein in an aqueous solvent and hydrolyzing the solubilized casein with an agent (e.g., a protease) that does not cleave the C6, C7 and C12 peptides. The resulting hydrolysate is then fractionated such that a fraction is obtained that comprises at least 2.5% by weight of each of the C6, C7 and C12 peptides, more preferably, at least 2.5% by weight of each of C6 and C7 and at least 4% by weight of C12. Most preferably a fraction is obtained that comprises at least 3.0% by weight of C6 and C7 and at least 6% by weight of C12.

Casein suitable for use in the present invention can be derived from any of a variety of sources. Advantageously, the casein contains both $\alpha_{s1}$ and $\beta$ casein fractions. For example, acid casein, salts of casein, and rennet casein can be used. In addition casein streams (e.g., liquid process streams resulting from dairy/dairy product processing) can be used.

In accordance with the present method, an aqueous solution of the casein is prepared and to that solution an agent is added that hydrolyzes the casein but does not cleave the C6, C7 and C12 peptides. Suitable agents include proteolytic enzymes (proteases) such as trypsin or trypsin like proteases (e.g., proteases having the specificity of that of trypsin). Advantageously, the proteolytic enzyme is selected from those typically used as a reagent purified for pharmaceutical applications or for use as a food additive. Preferably, the proteolytic enzyme is free from other residual enzymes, especially, residual proteolytic enzymes. The agent is incubated with the casein under conditions such that hydrolysis is effected.

The resulting casein hydrolysate is fractionated so that a fraction is obtained that comprises at least 3% by weight of each of the C6, C7 and C12 peptides, more preferably, at least 3% by weight of the C6 and C7 peptides and at least 6% by weight of the C12 peptide the percentages being calculated as the weight of the peptide per weight of dry matter multiplied by 100). The fractionation can be carried out on the basis of molecular size alone or on the basis of molecular size and ionic strength (charge). Techniques suitable for use in fractionating the hydrolyzed casein on the basis of size include membrane fractionation, such as ultra- or or nano-membrane filtration. Nanofiltration can also be used to effect charge separation since nanofiltration membranes tend to have high concentrations of negative charge on the membrane surface. Fractionation on the basis of molecular size and charge can be carried out using electrodialysis techniques.

Other bases for fractionation include hydrophobicity (e.g., using hydrophobic interaction chromatography or solvent extraction) and biological activity (e.g., using affinity chromatography).

The product of the present process can be concentrated, for example, by evaporation. The product can be stored and/or formulated as a concentrate or it can be evaporated to dryness.

The foregoing provides a general description of the invention. The following is a more detailed description of a preferred embodiment and includes examples of specific operating parameters.

In accordance with a preferred embodiment of the invention, casein can be solubilized in water at a concentration of about 8–13 weight % (i.e., weight of casein/weight of solution times 100—weight of solution=weight of water plus weight of casein) and at about 38–66° C. The pH of the casein solution can be adjusted to about 5.8–7.1 using, for example, 50% (w/v) sodium hydroxide and/or 45% (w/v) potassium hydroxide. The resulting product can be subsequently batch heated to about 77–88° C. and held at that temperature for about 30–90 minutes or the product can be heated to 77–88° C. with a heat exchanger and held 3 minutes at temperature before cooling with a second heat exchanger to 35–41° C. Following this heat treatment, the casein solution car be cooled to about 35–41° C. and the pH further adjusted to about 7.0–7.6 (preferably 7.4–7.6) with, for example, about 50% (w/v) sodium hydroxide and/or about 45% (w/v) potassium hydroxide.

A proteolytic enzyme, such as trypsin, can then be added to the casein solution at a concentration of, for example, about 0.05–3.0 weight % (i.e., weight of enzyme/weight of casein times 100). Hydrolysis is allowed to proceed for, for example, about 2 to 6 hours. Advantageously, the average molecular weight of the resulting hydrolysate is 4500–8000 Da. The enzyme is then inactivated, for example, by heat treatment at about 82–110° C. for about 3–90 minutes.

The hydrolysate can then be held in bulk at about 88–96° C. for about 30–120 minutes (preferably, 60–75 min) so that the hydrolysate agglomerates (that is, the molecular weight increases by at least 10% (e.g., to about 5500 Da)) (molecular weights being determined using the method shown in FIG. 1). Subsequently, the hydrolysate can be cooled to about 49–60° C. and the pH again adjusted to about 5.5–10 using, for example, concentrated HCl or 50% (w/v) NaOH and/or 45% (w/v) KOH, as appropriate.

Fractionation can then be carried out with, for example, ultrafiltration and/or nanofiltration membranes. In accordance with this approach, the hydrolysate can be fractionated not only by size exclusion but also on the basis of ionic strength by pH adjustments prior to ultrafiltration or nanofiltration (see FIG. 2). Membranes suitable for use include those having a molecular weight cutoff of 1500–7500 and, for example, a spiral wound configuration (examples of suitable membranes include HFK-328 from Koch Membrane Systems and AES-5K from PTI Advanced Filtration (10350 Barnes Canyon Road, San Diego, Calif. 92131)). The fractionation process can be carried out at about 49–60° C. and at a pH in the range of about 5.5–10. When performing ultrafiltration nanofiltration, continuous diafiltration from 200–600% is preferred (about 400% being more preferred) (see FIG. 2). Typically, the permeate of the ultrafiltration has an average molecular weight of 1400–3000 Da.

Use of ultrafiltration and/or nanofiltration (UF/NF) membranes can result in concentration of the C6, C7, and C12 peptides to at least 0.1% by weight of each of the peptides, at least 2.5% being preferred, and at least 3% C6 and C7 and at least 4% C12 being more preferred and at least 3% C6 and C7 and at least 6% C12 being most preferred. (Prior to ultrafiltration, typical percentages of the ACEI peptides are as follows: less than 2% for C12 and less that 1% for C6 and C7).

At this point, the C6, C7, and C12 peptides can be further purified with the use of, for example, electrodialysis equipment modified to hold ultrafiltration and/or nanofiltration membranes. When using membranes in conjunction with electrodialysis, the cell can have the following configuration: Anode|Anode comparatment|CEX membrane|Product compartment|UF/NF membrane|Feed compartment|UF/NF membrane|Product compartment|AEX membrane|Cathoode compartment|Cathode.

Permeate generated from ultrafiltration and/or nanofiltration and/or electrodialysis processing of the hydrolysate can be concentrated, for example, by RO to greater than 15% and/or by evaporation to greater than 40% total solids (percentage expressed as the weight of total dry solids/per weight of solution multiplied by 100). Concentrated permeates can be subjected to a final pH adjustment to about 6.0–7.5 using, for example, HCl or NaOH and/or KOH, as appropriate depending on the formulation in which the final product will be used. The solution can then dried, for example, by spray drying or lyophilization.

Typically, yields of ACEI peptides obtained using the method of the present invention are at least 6%, preferably, at least 8%, more preferably, at least 10% (% calculated as dry weight of ACEI peptides per dry weight of starting casein raw material multiplied by 100).

The dosage form of the product produced in accordance with the present invention can be any form that is acceptable for pharmaceutical or food use. For example, the product can be in a form suitable for oral administration (e.g., as a beverage, tablet, yogurt, confection, health snack bar, condiment, etc), or for administration by intubation. The product can be present in the dosage formulation, for example, at 1 to 10 weight %, preferably, 0.1 to 1 weight % based on the total weight of the peptides per weight of formulation.

The amount of the product of the present invention administered can be sufficient to treat or prevent circulatory diseases, particularly, hypertension. That amount will vary, for example, with the patient and the formulation used. Advantageously, the amount administered is 50 mg to 2 g of the ACEI peptides per day, preferably 100–200 mg per day. An optimum amount can be readily determined by one skilled in the art.

Certain aspects of the present invention are described in greater detail in the non-limiting Examples that follow. The ultrafiltration membranes used were HFK-328 membranes from Koch Membrane Systems, 850 Main Street, Wilmington, Mass. 01887; the ultrafiltration unit used was a Separatech Pilot Plant 25/50 m2 ultra filtration unit which holds 4–8 3.8" dia.×38" length spiral wound membranes, SeparaTech Div. of Ionics, 65 Grove Street, Watertown, Mass. 02272; agitation was effected using a full sweep agitator w/baffles 2 hp. motor @ 20–35 rpm; the digester tanks were from Waukesha Cherry-Burrell, 575 E. Mill Street, Little Falls, N.Y. 13365; the reverse osmosis unit was a Niro Pilot Plant Reverse Osmosis Unit, Niro Filtration Div., Niro Hudson, Inc., 1600 County Road F, Hudson, Wis., which holds 2 3.8" dia.×38" length spiral wound membranes; max. 600 psi. design pressure and reverse osmosis membranes were HTRO 3838 3.8" dia. 38" length, 4.83 m2/module, Dow FilmTec Corp., 7200 Ohms Lane, Edina, Minn. 55439; and the spray dryer was a Niro P6.3 Tower Spray Drier, Niro, Inc., 9165 Rumsey Road, Columbia, Md. 21045. (Manufacturers of equipment used in Examples 5 and 6 differed from those described above.)

EXAMPLE 1

Acid casein was dissolved in deionized water with agitation at 43° C. to make a 10% (w/v) solution. The pH was adjusted from 4.53 to 6.93 with 50% NaOH. Once the pH adjustment was completed, the casein solution was heated at 82° C. for 3 minutes and then cooled to 37° C. A final pH adjustment was made to 7.53 with 50% NaOH and trypsin was added at a 1:2000 enzyme:substrate ratio.

The hydrolysis was allowed to proceed for 4 hrs until the average MW of the casein was reduced to <5000 Da (determined using the method described in FIG. 1). At this time, the hydrolysis reaction was terminated with a second heat treatment at 104° C. for 3 minutes and cooled to 88° C. The hydrolysate was held batchwise prior to ultrafiltration with agitation at 88° C. until the hydrolysate agglomerated and the average molecular weight increased by at least 10% (e.g., to >5500 Da) (molecular weight determined using the method described in FIG. 1).

Immediately prior to ultrafiltration, the temperature of the hydrolysate was decreased to 60° C. and the pH was adjusted from 6.91 to 7.21 using 50% NaOH. When the ultrafiltration was started, it was allowed to run in a complete recirculation mode for 15 minutes. After recirculation, diafiltration was begun immediately. The water used for diafiltration was deionized. The membranes used were from Koch (HFK-328, 5000 molecular weight cutoff). (For details see FIGS. 2A–2D.)

As difiltration progressed, the average MW of the permeate increased from >1400 Da to >2200 Da. A reverse osmosis membrane unit was used to concentrate the permeate from <1.0% total solids to >13% total solids (total solids determined using a Mettler PM100 Analytical Balance, Mettler LP16 Infrared Moisture Analyzer, Mettler Toledo, 1900 Polaris Parkway, Columbus, Ohio. 43240). The ACEI product was then spray dried. The final yield of this process was 10.5%. Analysis of the final ACEI peptides was as follows: C12=9.07%, C6=3.96%, C7=3.97% (% peptides determiend using method shown in FIG. 3), MW=1825 (determined using method shown in FIG. 1), IC50=38 $\mu$M (determined as descirbed by Karaki et al, Comp. Biochem. Physiol., 96C, 367 (1990)).

EXAMPLE 2

Acid casein was dissolved in deionized water with agitation at 43° C. to make a 10% (w/v) solution. The pH was adjusted from 4.54 to 7.07 with 50% NaOH. Once the pH adjustment was completed, the casein solution was heated at 82° C. for 3 minutes and then cooled to 37° C. A final pH adjustment was made from 6.48 (after heating) to 7.54 with 50% NaOH and the enzyme was added at a 1:2000 enzyme:substrate ratio.

The hydrolysis was allowed to proceed until the average molecular weight of the casein was reduced to <5000 Da (determined as described in FIG. 1). At this time, the hydrolysis reaction was terminated with a second heat treatment at 104° C. for 3 minutes and cooled to 60° C. The hydrolysate was held batchwise prior to ultrafiltration with agitation at 60° C.

Immediately prior to ultrafiltration, the temperature of the hydrolysate was 60° C. and the pH was adjusted from 6.95 to 7.02 using 50% NaOH. When the ultrafiltration was started, it was allowed to run in a complete recirculation mode for 15 minutes (see FIG. 2). After recirculation, diafiltration was begun immediately. The water used for diafiltration was deionized. The membranes used were from Koch (HFK-328, 5000 MWCO). (For details see FIGS. 2A–2D.)

As difiltration progressed, the average molecular weight of the permeate increased from >1400 Da to >2200 Da. A reverse osmosis membrane unit was used to concentrate the permeate from <1.0% total solids to >13% total solids (total solids determined as described in Example 1). Then this ACEI product was split—part was spray dried and the other part was lyophilized. The drying method does not seem to have an effect on the final ACEI concentration. The final yield of this process was 11.5%. Analysis of the final ACEI peptides was as follows: C12=6.84%, C6=3.97%, C7=4.16%, MW=1850, IC50=75 $\mu$M. (See Example 1 and FIG. 3.).

EXAMPLE 3

Acid casein was dissolved in deionized water with agitation at 43° C. to make a 10% (w/v) solution. The pH was adjusted from 4.56 to 7.02 with 50% NaOH. Once the pH adjustment was completed, the casein solution was heated at 82° C. batchwise for 30 minutes and then cooled to 37° C. A final pH adjustment was made to 7.48 with 50% NaOH and the enzyme was added at a 1:2000 enzyme:substrate ratio.

The hydrolysis was allowed to proceed until the average molecular weight of the casein was reduced to <5000 Da (see FIG. 1). At this time, the hydrolysis reaction was terminated with a batchwise second heat treatment at 104° C. for 3 minutes and cooled to 88° C. The hydrolysate was held batchwise prior to ultrafiltration with agitation at this temperature until the hydrolysate agglomerated and the average molecular weight increased to >5500 Da (see FIG. 1).

Immediately prior to ultrafiltration, the temperature of the hydrolysate was decreased to 60° C. and the pH was adjusted from 6.82 to 9.86 using 50% NaOH. When the ultrafiltration was started, it was allowed to run in a complete recirculation mode for 15 minutes (see FIG. 2). After recirculation, diafiltratior was begun immediately. The water used for diafiltration was deionized. The membranes used were from Koch (HFK-328, 5000 molecular weight cutoff). (For details see FIGS. 2A–2D.)

A reverse osmosis (RO) membrane unit was used to concentrate the permeate from <1.0% total solids to >13% total solids (total solids determined as described in Example 1). The ACEI product was then lyophilized. Analysis of the final ACEI peptides is as follows: C12=6.7%, C6=2.4%, C7=4.6%, MW=1144, IC50=103 $\mu$M. (See Example 1 and FIG. 3.)

EXAMPLE 4

Acid casein was dissolved in deionized water with agitation at 43° C. to make a 10% (w/v) solution. The pH was adjusted from 4.56 to 7.02 with 50% NaOH. Once the pH adjustment was completed, the casein solution was heated at 82° C. batchwise for 30 minutes and then cooled to 37° C. A final pH adjustment was made to 7.48 with 50% NaOH and the enzyme was added at a 1:2000 enzyme:substrate ratio.

The hydrolysis was allowed to proceed until the average molecular weight of the casein was reduced to <5000 Da (see FIG. 1). At this time, the hydrolysis reaction was terminated with a batchwise second heat treatment at 104° C. for 3 minutes and cooled to 88° C. The hydrolysate was held batchwise prior to ultrafiltration with agitation at this temperature until the hydrolysate agglomerated and the average molecular weight increased to >5500 Da (see FIG. 1).

Immediately prior to ultrafiltration the temperature of the hydrolysate was decreased to 60° C. and the pH was adjusted from 6.82 to 6.0 using $H_2SO_4$. When the ultrafiltration was started, it was allowed to run in a complete recirculation mode for 15 minutes (see FIG. 2). After recirculation, diafiltration was begun immediately. The water used for diafiltration was deionized. The membranes used were from Koch (HFK-328, 5000 molecular weight cutoff). (For details see FIGS. 2A–2D.)

A reverse osmosis membrane unit was used to concentrate the permeate from <1.0% total solids to >13% total solids (total solids determined as described in Example 1). The ACEI product was then lyophilized. Analysis of the final ACEI peptides was as follows: C12=7.5%, C6=3.0%, C7=2.6%, MW=1210, IC50=103 $\mu$M. (See Example 1 and FIG. 3.).

EXAMPLE 5

Acid casein was dissolved in deionized water with good agitation at 43° C. to make a 10% (w/v) solution. The pH was adjusted from 4.56 to 7.02 with 50% NaOH. Once the pH adjustment was completed, the casein solution was heated at 82° C. batchwise for 30 minutes and then cooled to 37° C. A final pH adjustment was made to 7.48 with 50% NaOH and the enzyme was added at a 1:2000 enzyme:substrate ratio.

The hydrolysis was allowed to proceed until the average MW of the casein was reduced to <5000 Da (see FIG. 1). At this time, the hydrolysis reaction was terminated with a batchwise second heat treatment at 104° C. for 3 minutes and cooled to 88° C. The hydrolysate was held batchwise prior to ultrafiltration with agitation at this temperature until the hydrolysate agglomerated and the average molecular weight increased to >5500 Da (see FIG. 1).

Immediately prior to ultrafiltration, the temperature of the hydrolysate was decreased to 60° C. and the pH was adjusted from 6.82 to 6.0 using $H_2SO_4$. When the ultrafiltration was started, it was allowed to run in a complete recirculation mode for 15 minutes (see FIG. 2). After recirculation, diafiltration was begun immediately. The water used for diafiltration was deionized. The membranes used were from Koch (HFK-328, 5000 molecular weight cutoff). (For details see FIGS. 2A–2D.).

A reverse osmosis membrane unit was used to concentrate the permeate from <1.0% total solids to >13% total solids (total solids determined as described in Example 1). The ACEI product was then lyophilized. Analysis of the final ACEI peptides was as follows: C12=7.5%, C6=3.0%, C7=2.6%, MW=1210, IC50=103 $\mu$M. (See Example 1 and FIG. 3.).

EXAMPLE 6

Acid casein was dissolved in deionized water with agitation at 43° C. to make a 10% (w/v) solution. The pH was adjusted from 4.56 to 7.02 with 50% NaOH. Once the pH adjustment was completed, the casein solution was heated at 82° C. batchwise for 30 minutes and then cooled to 37° C. A final pH adjustment was made to 7.48 with 50% NaOH and the enzyme was added at a 1:2000 enzyme:substrate ratio.

The hydrolysis was allowed to proceed until the average molecular weight of the casein was reduced to <5000 Da (see FIG. 1). At this time, the hydrolysis reaction was terminated with a batchwise second heat treatment at 104° C. for 3 minutes and cooled to 88° C. The hydrolysate was held batchwise prior to ultrafiltration with agitation at this temperature until the hydrolysate agglomerated and the average molecular weight increased to >5500 Da (see FIG. 1).

Immediately prior to ultrafiltration, the temperature of the hydrolysate was decreased to 60° C. and the pH was adjusted from 6.82 to 6.0 using $H_2SO_4$. When the ultrafiltration was started, it was allowed to run in a complete recirculation mode for 15 minutes (see FIG. 2). After recirculation, diafiltration was begun immediately. The water used for diafiltration was deionized. The membranes used were from Koch (HFK-328, 5000 molecular weight cutoff). (For details see FIGS. 2A–2D.)

A reverse osmosis membrane unit was used to concentrate the permeate from <1.0% total solids to >16% total solids (total solids determined as described in Example 1). This ACEI concentrate was then nanofiltered. Analysis of the ACEI peptides prior to nanofiltration was as follows: C12=6.2%, C6=3.3%, C7=3.7%, MW=1491, IC50=N/A, Na=3.2%. (See Example 1 and FIG. 3.)

Before the start of diafiltration, the volume of ACEI concentrate was reduced 2 volumes (volume concentration reduction (VCR)=2) using the nanofiltration membranes (PCI AFC30) at 50° C. and a feed pressure of 40 bar.

Following this concentration and prior to diafiltration, the pH was 8.2. After diafiltration with deionized water, the final ACEI product was lyophilized. Final analysis of these peptides was as follows: C12=8.2%, C6=3.7%, C7=3.5%, MW=1488, IC50=N/A, Na=2.1%. (See Example 1 and FIG. 3.)

All documents cited above are hereby incorporated in their entirety by reference.

One skilled in the art will appreciate from a reading of this disclosure that various changes in form and detail can be made without departing from the true scope of the invention.

What is claimed is:

1. A method of preparing a composition comprising C6, C7 and C12 peptides, said method comprising:
   i) hydrolyzing solubilized casein with a protease that has a substrate specificity such that said protease does not cleave said C6, C7 and C12 peptides, and
   ii) holding the hydrolysate resulting from step (i) under conditions such that the average molecular weight of said hydrolysate resulting from step (i) increases by at least 10%,
   iii) adjusting the pH of the hydrolysate resulting from step (ii) to between 5.5 and 10, and
   iv) size fractionating the hydrolysate resulting from step (iii) under conditions such that at least one fraction is obtained that comprises at least 2.5% by weight of said C6 peptide, at least one fraction is obtained that comprises at least 2.5% by weight of said C7 peptide and at least one fraction is obtained that comprises at least 2.5% by weight of said C12 peptide.

2. The method according to claim 1 wherein said casein is an acid casein, a salt of casein or rennet-casein.

3. The method according to claim 1 wherein said protease is trypsin.

4. The method for according to claim 1 wherein said hydrolysis is carried out under conditions such that the average molecular weight of the resulting hydrosylate is from 4500–8000 Da.

5. The method according to claim 1 wherein the hydrolysate is fractionated using a membrane.

6. The method according to claim 5 wherein the hydrolysate is fractionated using ultrafiltration, nanofiltration or electrodialysis.

7. The method according to claim 6 wherein said hydrolysate is fractionated using ultrafiltration and the permeate of said ultrafiltration has an average molecular weight of 1400–3000 Da.

8. The method according to claim 1 wherein, in step (iii), at least one fraction is obtained that comprises at least 3% by weight of said C6, at least one fraction is obtained that comprises at least 3% by weight of C7 and at least one fraction is obtained that comprises at least 6% by weight of C12.

* * * * *